(12) United States Patent
Marella

(10) Patent No.: US 10,517,337 B2
(45) Date of Patent: Dec. 31, 2019

(54) KNEE BRACE FOR WORKERS

(71) Applicant: Anthony Marella, Kenmore, NY (US)

(72) Inventor: Anthony Marella, Kenmore, NY (US)

(*) Notice: Subject to any disclaimer, the term of this patent is extended or adjusted under 35 U.S.C. 154(b) by 55 days.

(21) Appl. No.: 15/637,117

(22) Filed: Jun. 29, 2017

(65) Prior Publication Data

US 2019/0000160 A1 Jan. 3, 2019

(51) Int. Cl.
*A61F 5/00* (2006.01)
*A41D 13/06* (2006.01)
*A61F 5/01* (2006.01)
*A47C 16/04* (2006.01)

(52) U.S. Cl.
CPC ............ *A41D 13/065* (2013.01); *A47C 16/04* (2013.01); *A61F 5/0123* (2013.01); *A61F 2005/0181* (2013.01)

(58) Field of Classification Search
CPC ..... A41D 13/065; A41D 13/06; A61F 5/0123; A61F 5/0106; A61F 2005/0181; A47C 16/04
USPC .................................. 602/26; 2/2.5, 24, 22
See application file for complete search history.

(56) References Cited

U.S. PATENT DOCUMENTS

| | | | | |
|---|---|---|---|---|
| 2,432,565 A * | 12/1947 | Ferguson | ............ | A41D 13/0568 2/24 |
| 6,280,404 B1 * | 8/2001 | Morinaka | ............. | A61F 5/0102 602/16 |
| 8,752,214 B1 * | 6/2014 | Maldonado | .......... | A41D 13/065 2/22 |
| 2003/0127900 A1 * | 7/2003 | Chen | .................... | A41D 13/065 297/423.11 |
| 2010/0107291 A1 * | 5/2010 | Carter | ....................... | F41H 1/02 2/2.5 |
| 2011/0004134 A1 * | 1/2011 | Barrera | ..................... | A61F 5/01 602/16 |
| 2011/0094001 A1 * | 4/2011 | Maldonado | .......... | A41D 13/065 2/24 |
| 2013/0025017 A1 * | 1/2013 | Chen | ................... | A63B 71/1225 2/22 |
| 2016/0286871 A1 * | 10/2016 | Becirevic | ............. | A41D 13/065 |

* cited by examiner

*Primary Examiner* — Kim M Lewis
(74) *Attorney, Agent, or Firm* — Stadler IP Law PLLC

(57) ABSTRACT

A knee brace is provided that having a foot support assembly, a knee support assembly, and a calf engagement assembly. The foot support assembly is adjustable relative to the knee support assembly. The calf engagement assembly has a calf brace and is connectable to the foot support assembly and the knee support assembly with adjustment straps. The foot support assembly includes a foot adjustment plate that is connected to a shoe engagement component. The knee support assembly has a knee adjustment plate and has a multilayer pad, and a knee pad connector component connects the multilayer pad and the knee adjustment plate. The knee pad connector component can be connected such that the multilayer pad is in line with or offset relative to the knee pad connector, or the knee pad connector component can be replaced with right and left offset knee pad connector components.

11 Claims, 13 Drawing Sheets

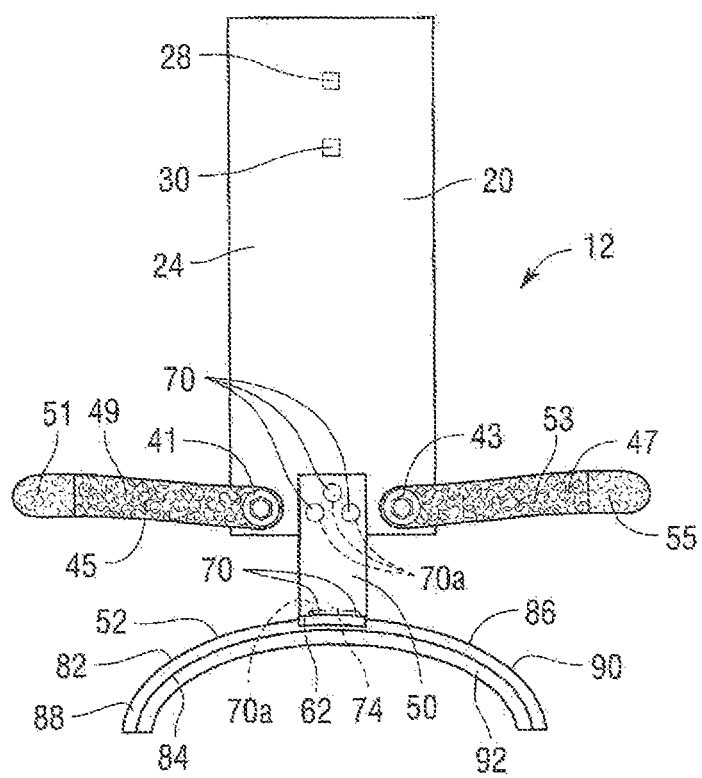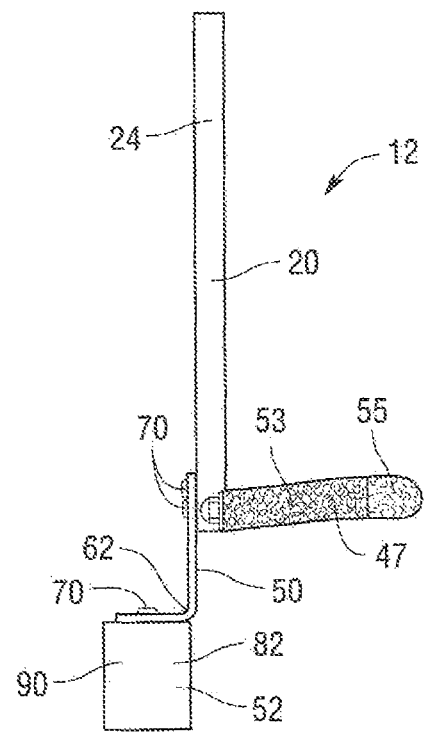

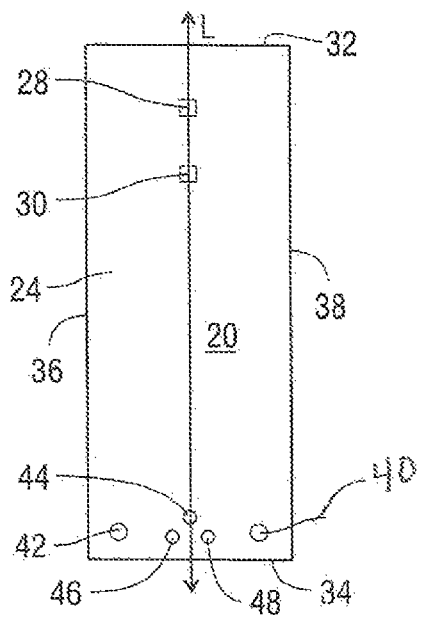
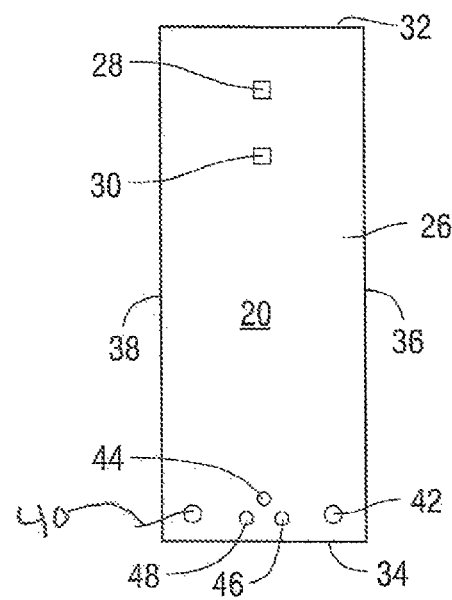
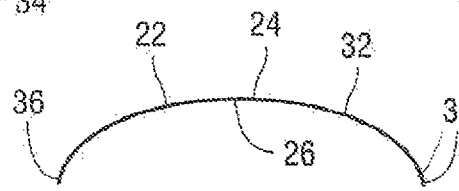
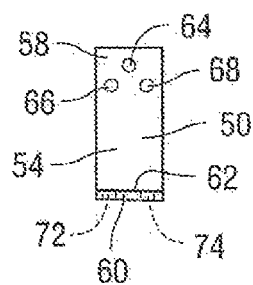
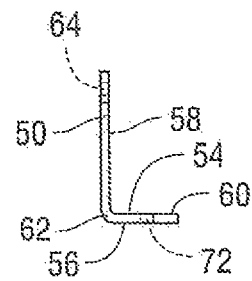
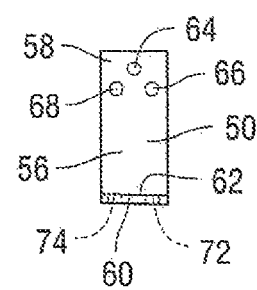
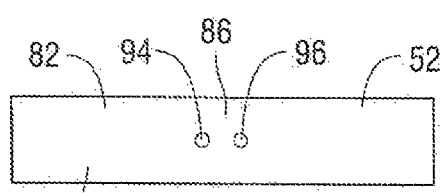
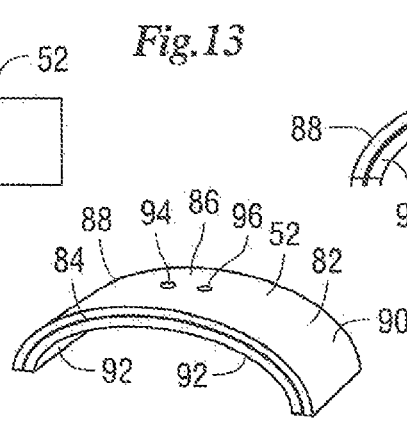
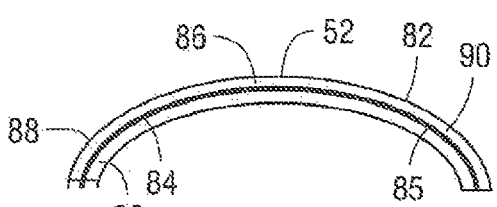

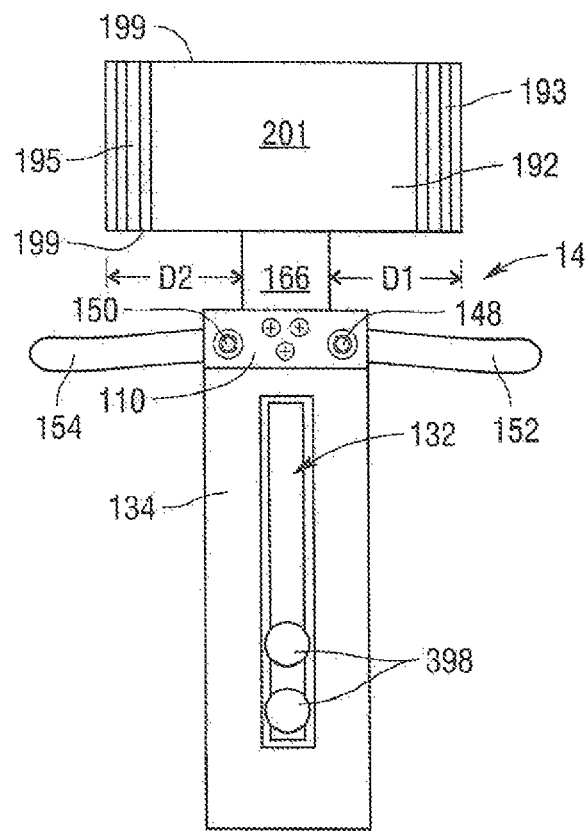
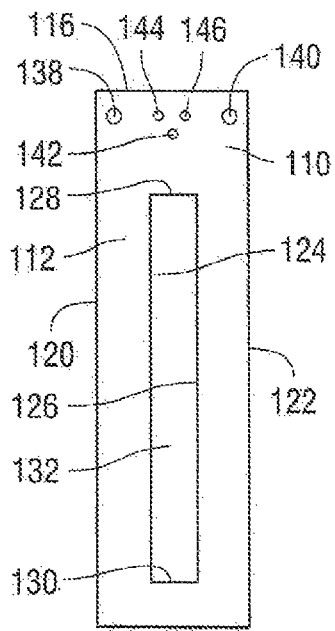
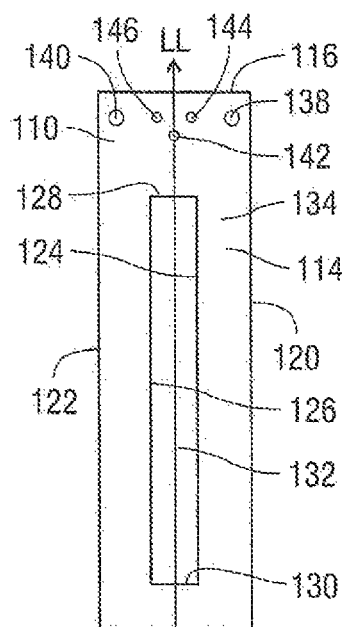
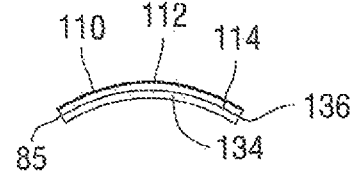
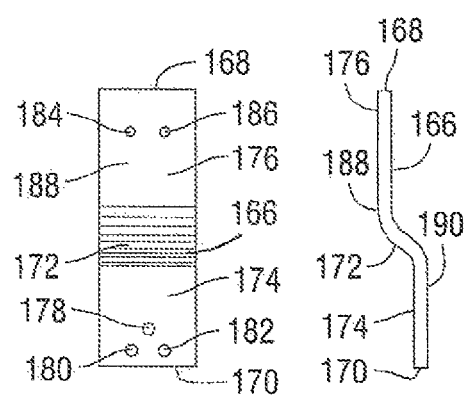

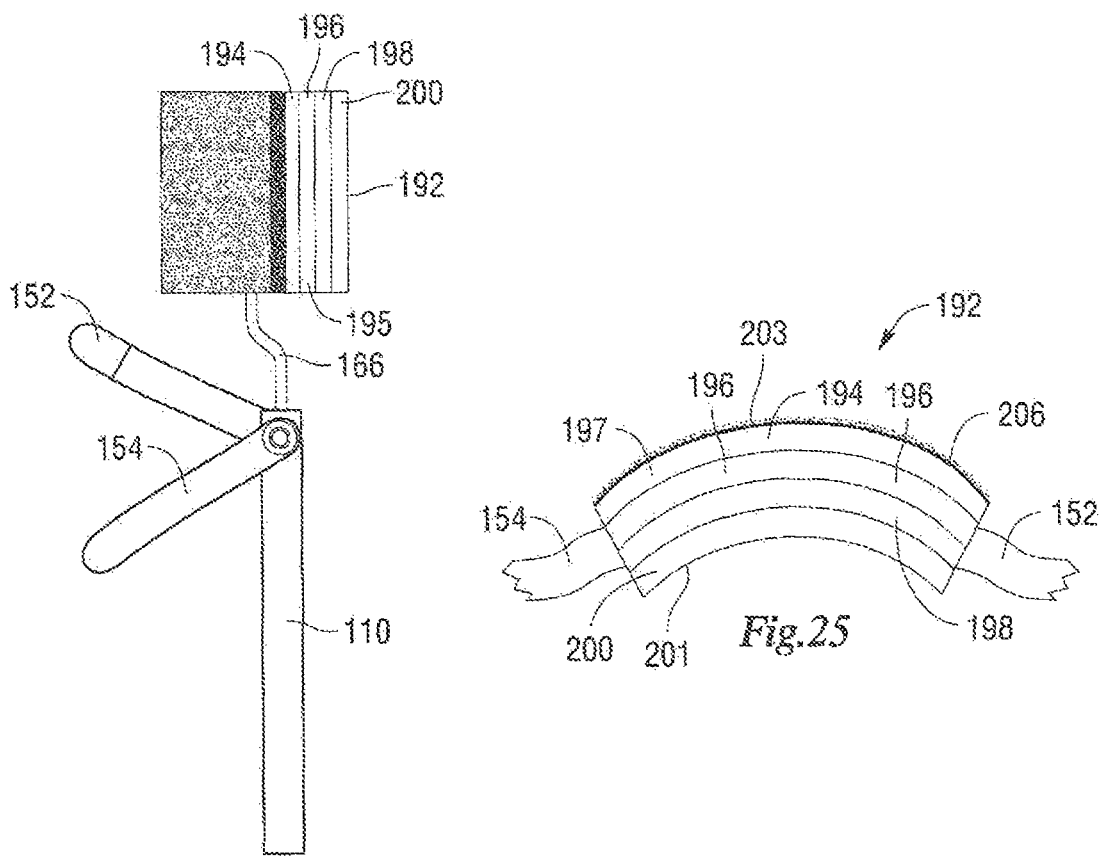
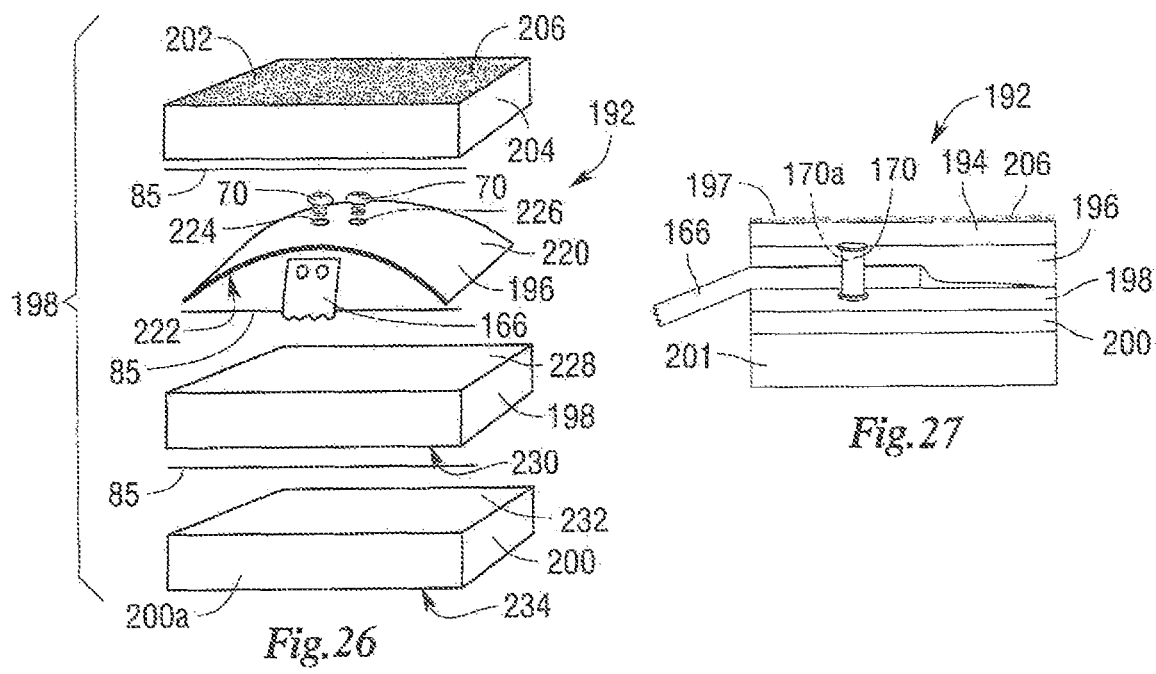

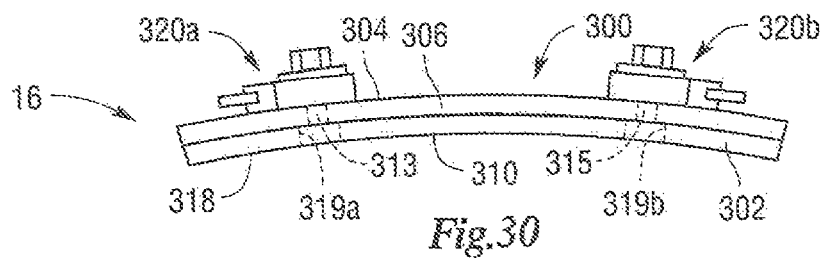
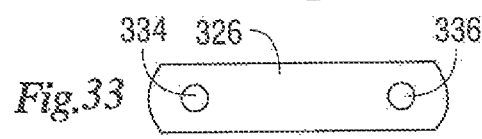
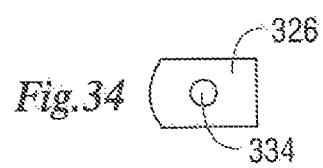
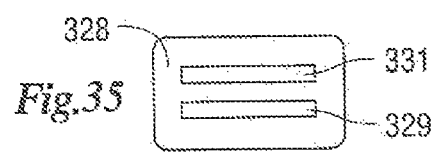
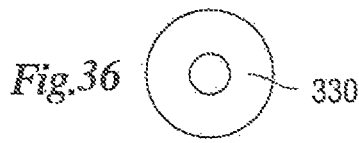
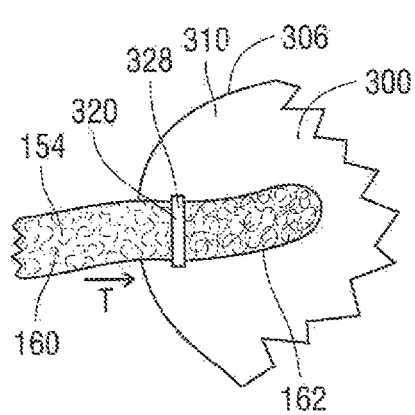
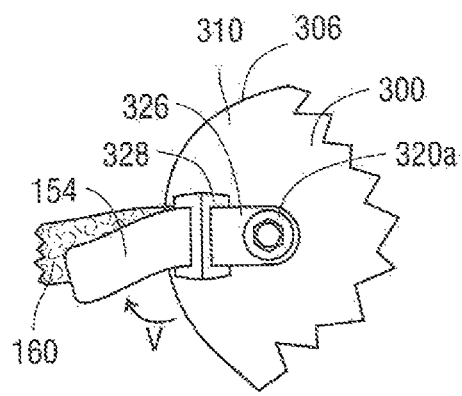

KNEE BRACE FOR WORKERS

BACKGROUND

Workers are often required to work some of the day, and in some instance all of the day, working on their hands and knees. For example, tile layers, bricklayers, masons, farm workers, carpenters and roofers spend a great deal of time working on their knees. This results in the knees of the workers being constantly subjected to wear and tear.

Over time many the workers start to experience knee pain. As the workers age and reach their fifty-year age mark the constant loads imposed on the knees becomes problematic. The knee problems the workers have can become quite serious over time and may require knee surgery in and attempt to correct the damage to the knee. It is estimated that nine out of ten workers end up retiring and leaving the field of construction due to knee problems.

As a solution to the problem of working on knees some workers use some form of a knee support device or pad designed to protect the knee. However, to date no such knee support devices have been successful. Three of the more significant problems these support devices have in common are sliding down the leg, shifting from side to side, and cutting off circulation in the leg and foot. These devices are designed in such a way that they end up providing little support and as a result workers are forced to return to working on their knees with no support, after having spent money on the knee support devices that did not produce satisfactory results What is need is a knee device that can be worn by workers to protect their knees that is easy to use, durable, that stays in place, allows for a full range of motion, and that is comfortable to wear throughout the day without the worker even knowing the device is being worn.

SUMMARY

A knee brace is provided that comprises a foot support assembly, a knee support assembly, and a calf engagement assembly. The foot support assembly is adjustable relative to the knee support assembly. The calf engagement assembly has a calf brace and the calf engagement assembly is connected to the foot support assembly and the knee support assembly with first, second, third and fourth adjustment straps.

The foot support assembly includes a foot adjustment plate and a shoe engagement component that is adapted to abut the shoe being worn by a worker. A connecting member connects the foot adjustment plate to the shoe engagement component. The knee support assembly has a knee adjustment plate and has a multilayer pad that is for supporting the knee of the worker when he or she kneels on the ground. The multilayer pad is connected to the knee adjustment plate with a knee pad connector component. The foot adjustment plate and knee adjustment plate are capable of being slid relative to one another through the use of adjustment bolt assemblies, such that a length of the knee brace can be expanded and contracted depending on the length of the leg of the worker. The adjustment bolt assemblies are capable of allowing the foot and knee adjustment plates to move relative to one another, and are capable of securing in place the foot and knee adjustment plates such that they are unable to slide relative to one another. The adjustment bolt assemblies are capable of being tightened so as to lock the foot and knee adjustment plates in place when the worker determines the length of the knee brace provides a comfortable fit. Extending from the foot and knee adjustment plates are first, second, third and fourth adjustment straps that are capable of engaging the calf engagement assembly to thus secure the knee brace to his or her leg.

The multilayer pad can be in line with the knee adjustment plate, that is, the multilayer pad is not offset relative to the knee adjustment plate. In another embodiment the knee pad connector components are offset relative to the multilayer pad such that one knee support assembly is suitable for use with the left knee and another knee brace assembly is suitable for use with the right knee. In another embodiment the knee pad connector component is replaced with a right offset knee pad connector component and a left offset knee pad connector component such that one knee support assembly is suitable for use with the left knee and the other knee brace assembly is suitable for use with the right knee.

BRIEF DESCRIPTION OF THE DRAWING FIGURES

FIG. 6 is a front view of a foot support assembly.

FIG. 7 is a right side view of the foot support assembly.

FIG. 8 is a front view of a foot adjustment plate.

FIG. 9 is a rear view of the foot adjustment plate.

FIG. 10 is a top view of the foot adjustment plate.

FIG. 11 is a front view of a connecting member.

FIG. 12 is a rear view of the connecting member.

FIG. 13 is a left side view of the connecting member.

FIG. 14 is a top view of a shoe engagement component.

FIG. 15 is a front view of the shoe engagement component.

FIG. 16 is a perspective view of the shoe engagement component.

Figure 17:
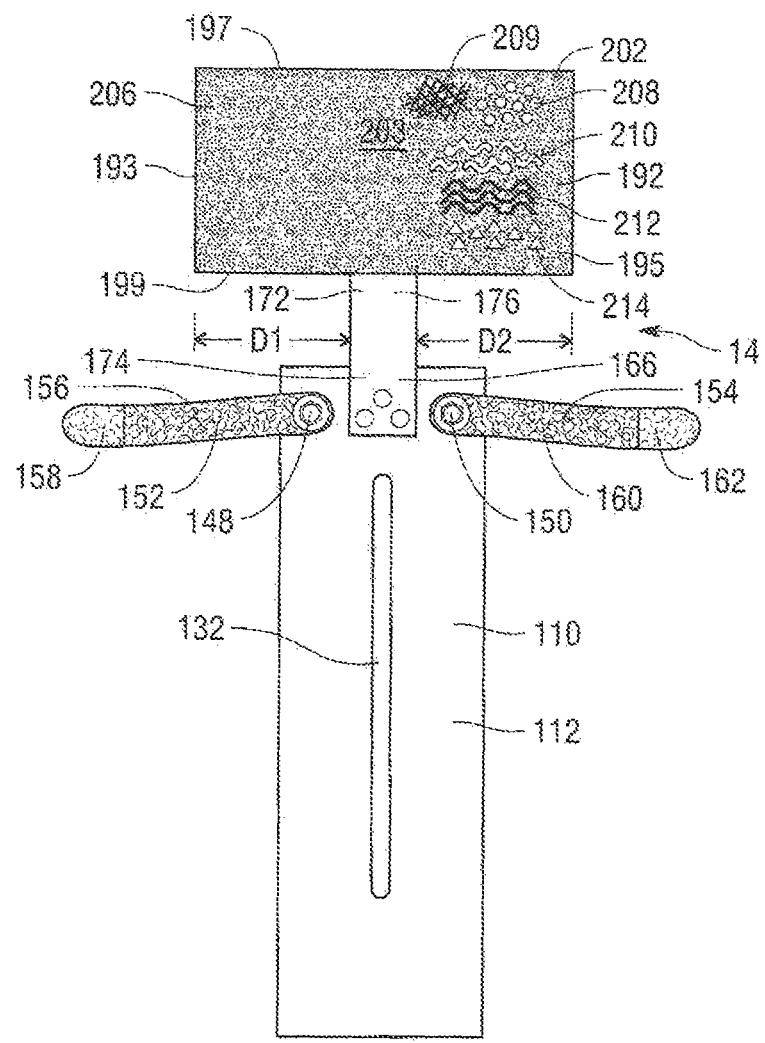
FIG. 17 is a front view of the knee support assembly.
Figure 17A:
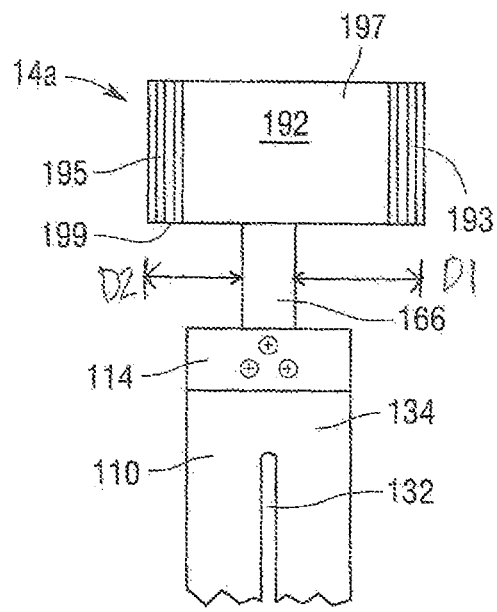
FIG. 17A is a front view of the knee support assembly wherein a multilayer pad is offset relative to a knee pad connector component.
Figure 17B:
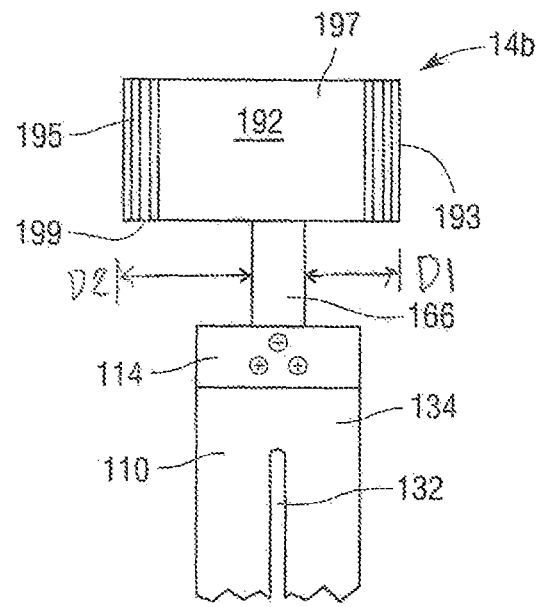
Figure 17C:
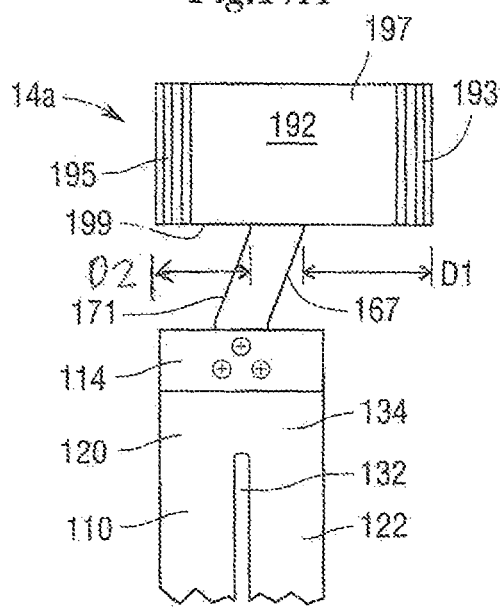

FIG. 17B a front view of the knee support assembly wherein the multilayer pad is offset relative to a knee pad connector component FIG. 17C is a front view of a right offset knee pad connector component that connects the multilayer pad to a knee adjustment plate.

Figure 17D:
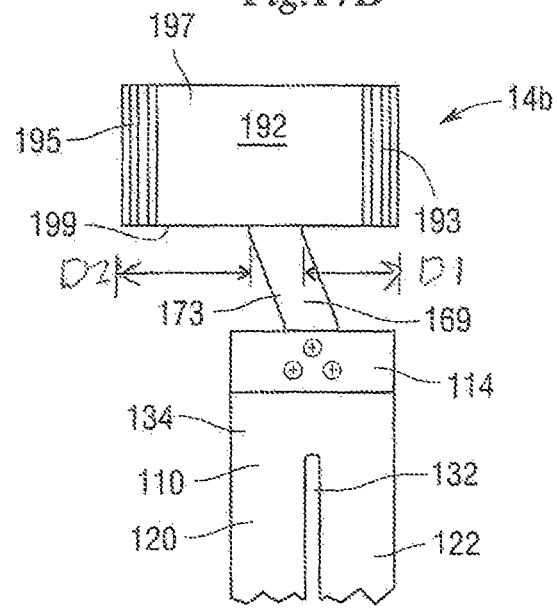

FIG. 17D is a front view of a left offset knee pad connector component that connects the multilayer pad to the knee adjustment plate.

Figure 17E:
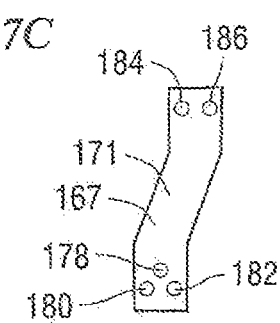

FIG. 17E is a front view of the right offset knee pad connector component.

Figure 17F:
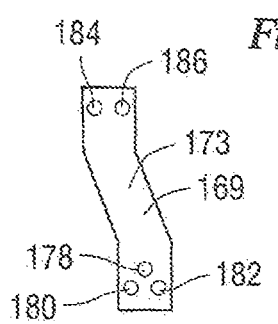

FIG. 17F is a front view of the left offset knee pad connector component.

FIG. 18 is a rear view of the knee support assembly.

FIG. 19 is a front view of the knee adjustment plate.

FIG. 20 is a rear view of the knee adjustment plate.

FIG. 21 is a top view of the knee adjustment plate.

FIG. 22 is a front of a knee pad connector component.

FIG. 23 is a side view of the knee pad connector component.

FIG. 24 is a side view of the knee support assembly.

FIG. 25 is a top view of the multilayer pad.

FIG. 26 is an expanded view of the multilayer pad.

FIG. 27 is a sectional view of the multilayer pad.

Figure 28:
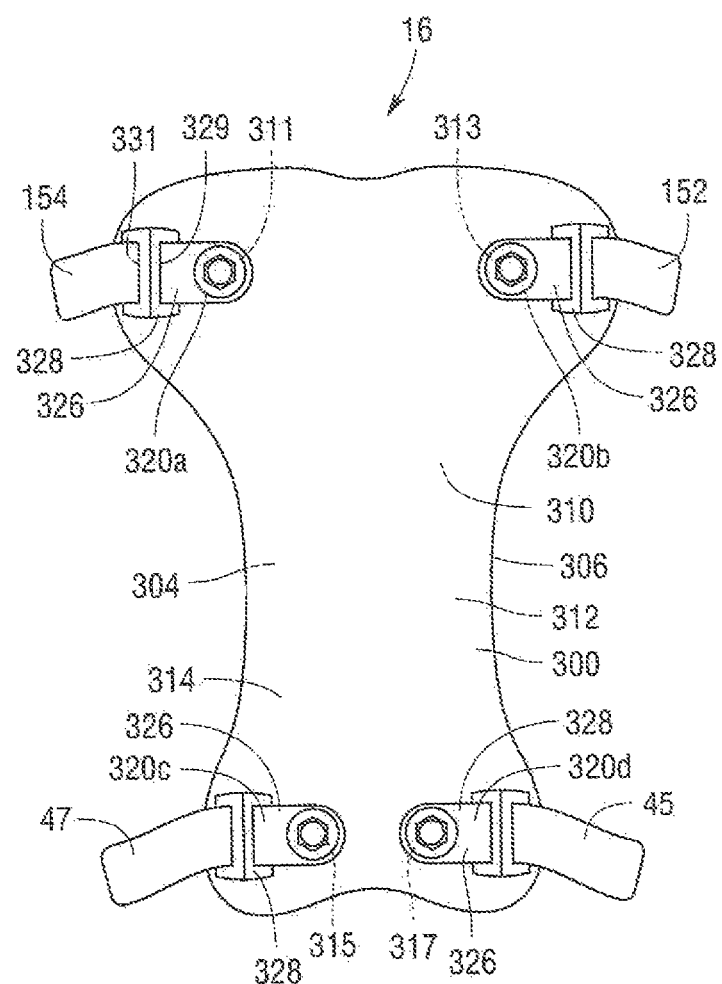

FIG. 28 is a front view of the calf engagement assembly.

Figure 29:
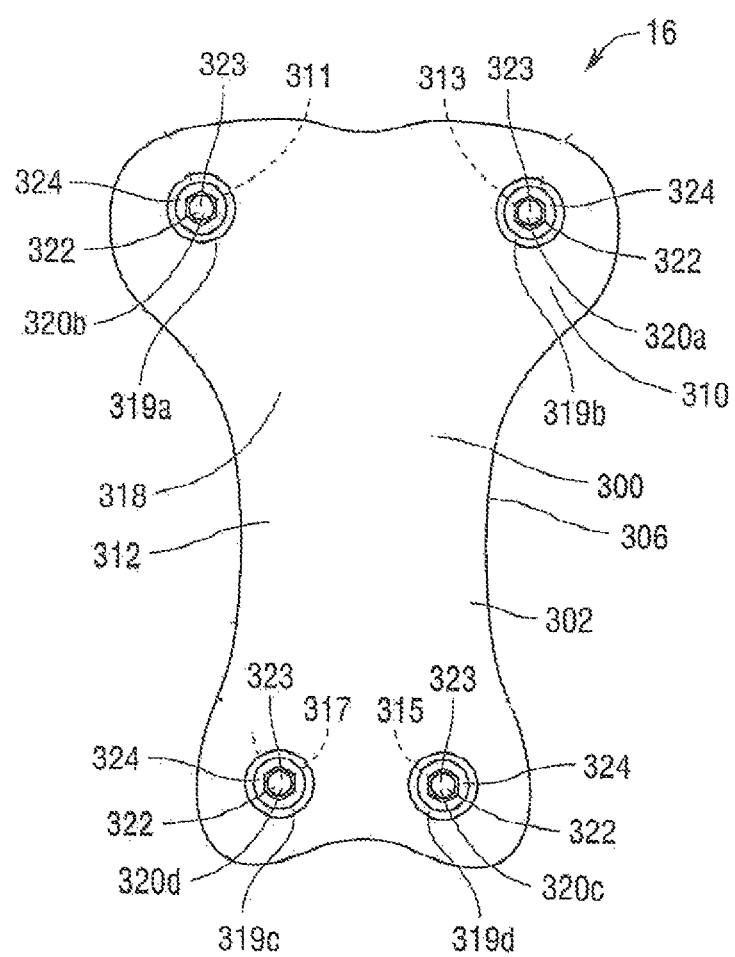

FIG. 29 is a rear view of the calf engagement assembly.

FIG. 30 is a top view of the calf engagement assembly.

FIGS. 31-37 show the components of the first strap connecting assembly.

FIG. 38 is a front view showing a fourth adjustment strap fitted in the first strap connecting assembly.

FIG. 39 is a front view showing the fourth adjustment strap folded on itself and secured to the first strap connecting assembly.

Figure 40:
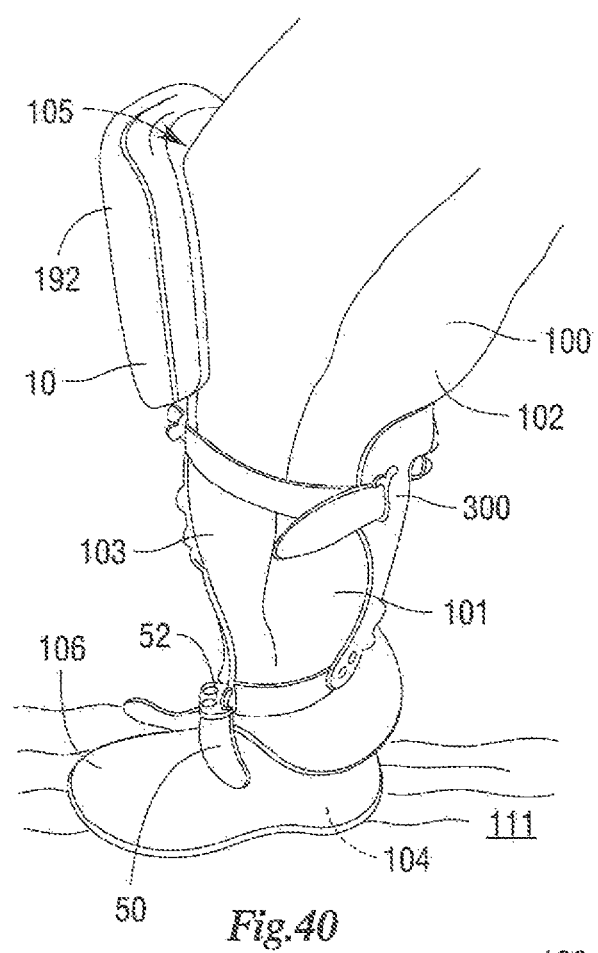
Figure 41:
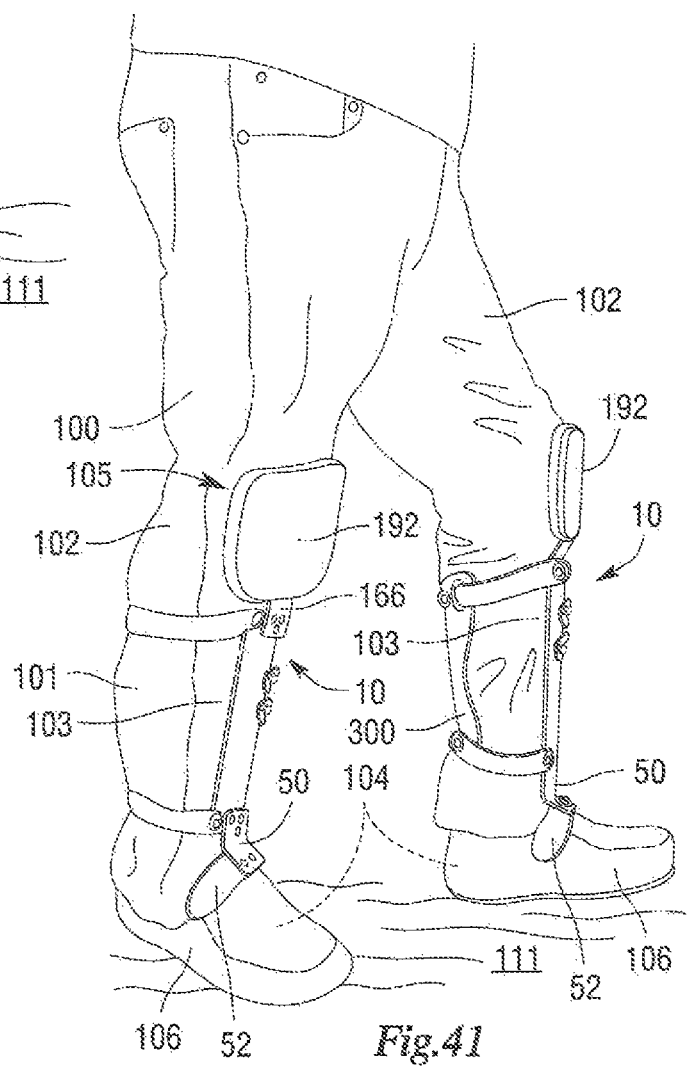

FIGS. 40-41 show the knee brace when worn by a worker.

DESCRIPTION

At the outset it is stated that in the variously described embodiments and/or structures herein, identical parts, surfaces and components are provided with like reference numerals.

Figure 1:
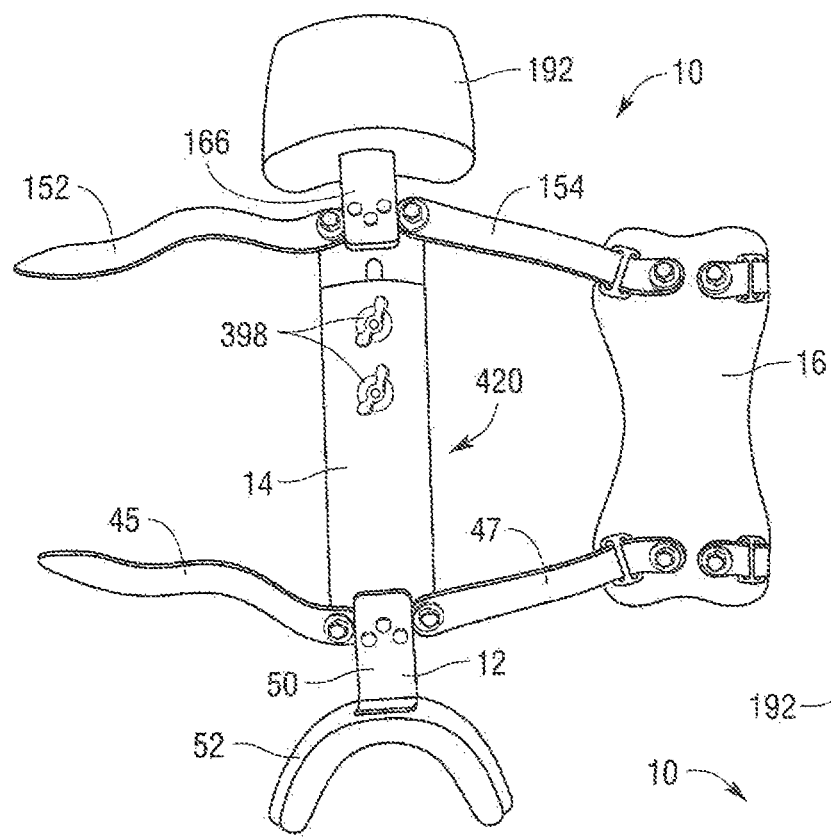
FIG. 1 is a front view of a knee brace prior to being installed on a leg of a worker.

A knee brace 10 is shown in FIG. 1 and the knee brace 10 is for use by a worker 100. Worker 100 can attach and detach the knee brace 10 from his or her legs 102, and the knee brace 10 is capable of being used when the worker 100 is walking or working on the ground 111 as shown in FIGS. 40-41.

Figure 2:
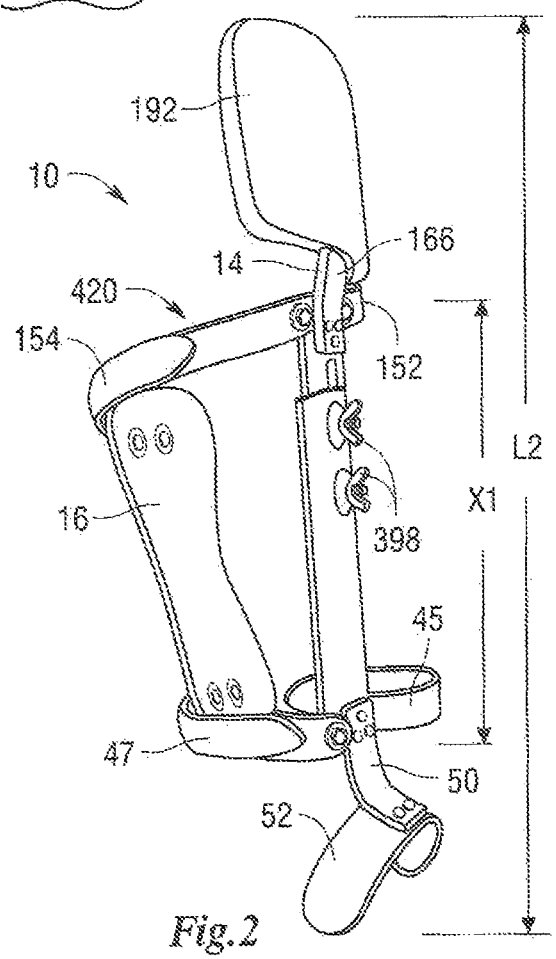
FIG. 2 is a right side view of the knee brace.
Figure 3:
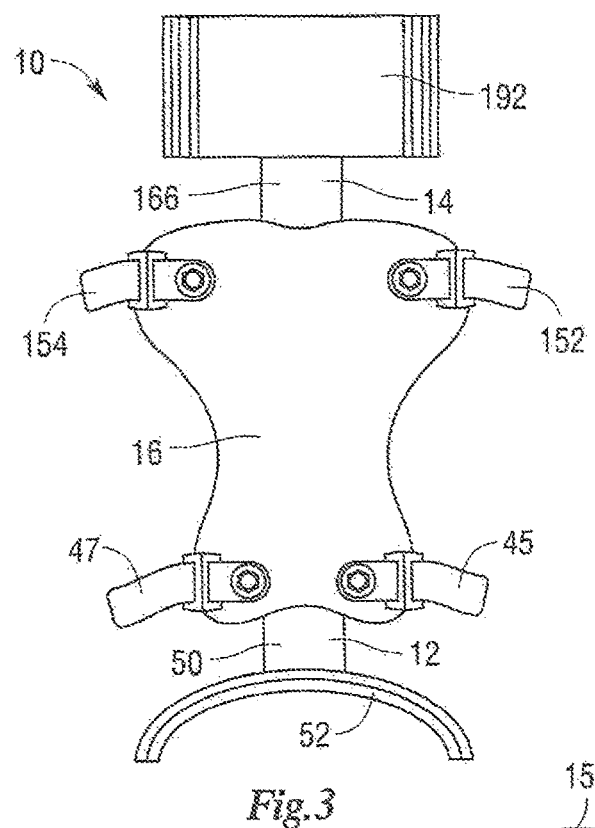
FIG. 3 is a rear view of the knee brace.

As shown in FIGS. 1 and 2 the knee brace 10 comprises a foot support assembly 12 that is operatively associated with a knee support assembly 14, and a calf engagement assembly 16, and the calf engagement assembly 16 is capable of being secured to and released from the foot support assembly 12 and the knee support assembly 14. FIG. 3 shows a front view of the calf engagement assembly 16.

Figure 4:
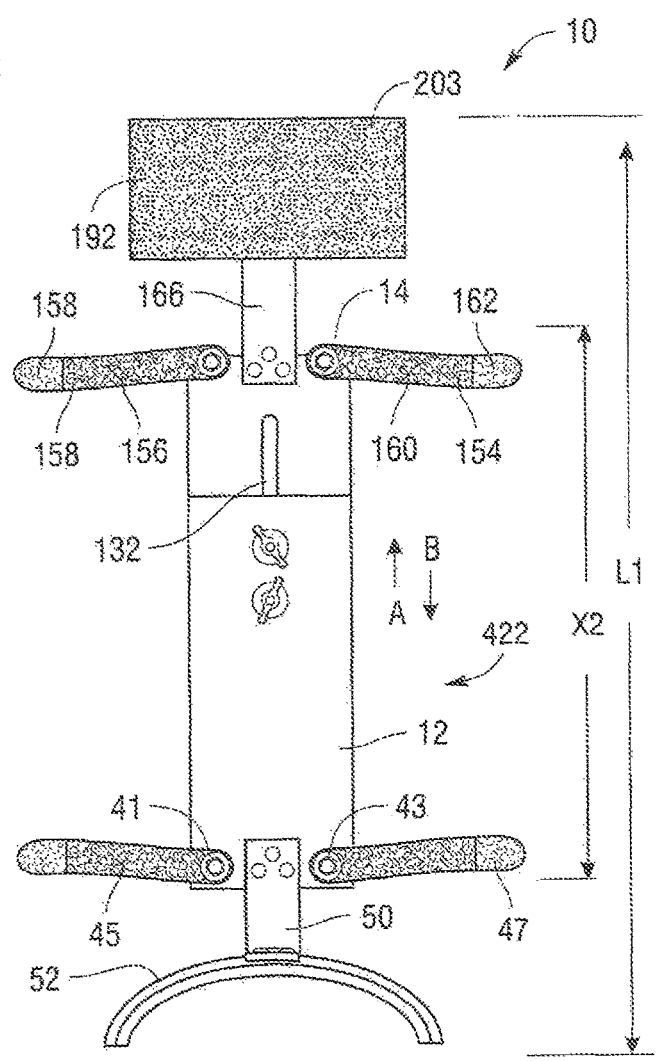
FIG. 4 is a front view of the knee brace when a calf engagement assembly is not shown for the sake of clarity.
Figure 5:
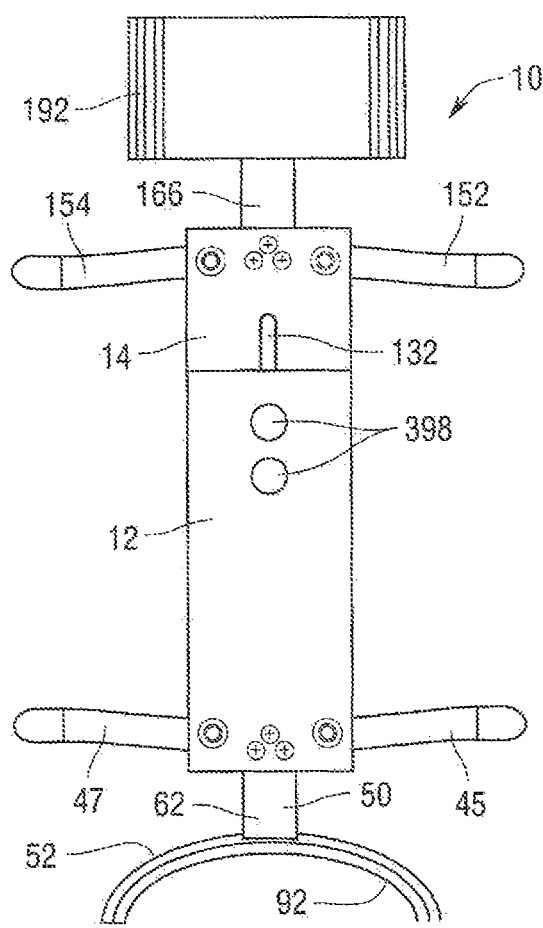
FIG. 5 is a rear view of the knee brace wherein the calf brace assembly is not shown for the sake of clarity.

FIG. 4 is a front view of the foot support assembly 12 and the knee support assembly 14 wherein the calf brace assembly 16 is not present. FIG. 5 is a rear view of the foot support assembly 12 and the knee support assembly 14 wherein the calf brace 16 is not present.

FIG. 6 is a front view of the foot support assembly 12, and FIG. 7 is a right side view of the foot support assembly 12. The foot support assembly 12 includes a foot adjustment plate 20 having opposed first and second foot adjustment plate surfaces 24, 26, as shown in FIGS. 6-10. In one embodiment and as shown in FIG. 10, the first adjustment plate surface 24 is convex and the second foot adjustment surface 26 is concave. In another embodiment the foot adjustment plate 20 is planar, that is it is flat. As shown in FIG. 8, the foot adjustment plate 20 also defines a pair of spaced apart square shaped adjustment bolt openings 28, 30. In another embodiment the pair of spaced apart openings may be round or circular. A first longitudinal axis designated L in FIG. 8 extends through the foot adjustment plate 22 and through the first and second adjustment share shaped adjustment bolt openings 28, 30. The food adjustment plate 20 has opposed first and second end edges 32, 34, and opposed first and second side edges 36, 38. The foot adjustment plate 20 also defines first and second strap bolt openings 40, 42, wherein the first strap bolt opening 40 is positioned proximal to the second edge 34 and the first side edge 36, and the second strap bolt opening 42 is positioned proximal to the second edge 34 and the second side edge 38. The foot adjustment plate 20 also defines first, second and third foot adjustment plate fastener openings 44, 46, 48 that are disposed between the first and second strap bolt openings 40, 42, and proximal the second edge 34 as shown in FIGS. 8 and 9. The first, second and third foot adjustment plate fastener openings 44, 46, 48 are spaced from one another and in one embodiment they together form the shape of a triangle. The foot adjustment plate 20 may be made of metal, aluminum, sheet steel, plastic, fiberglass and other suitable materials. As best shown in FIG. 6, first and second strap bolts 41, 43 are provided, and first strap bolt 41 extends through the first strap bolt opening 40 and through a first adjustment strap 45 and secures the first adjustment strap 45 to the foot adjustment plate 20. The second strap bolt 43 extends through the second strap bolt opening 42 and through a second adjustment strap 47 securing the second adjustment strap 47 to the foot adjustment plate 20. Each of the first and second adjustment straps 45, 47 are structurally the same and the first adjustment strap 45 has a loop portion 49 and a hook portion 51, and the second adjustment strap 47 has a loop portion 53 and a hook portion 55.

As shown in FIGS. 6, 7 and 11-13, the foot support assembly 12 further includes a connecting member 50 that connects the foot adjustment plate 20 to a shoe engagement component 52. The connecting member 50 has opposed first and second connecting member surfaces 54, 56, and has a first portion 58 that meets with a second portion 60 at a bent portion 62. The bent portion 62 results in the first connecting member surface 54 being folded in upon itself as shown in FIG. 13. The first portion connecting 58 of the connecting member 50 defines first, second and third engagement component openings 64, 66, 68 that are spaced from one another in a manner identical to the spacing of the first, second and third foot adjustment plate fastener openings 44, 46, 48, such that the first, second and third engagement component openings 64, 66, 68 are capable of being aligned with the first, second and third foot adjustment plate fastener openings 44, 46, 48. Fasteners 70 are inserted in the aligned first, second and third engagement component openings 64, 66, 68 and first, second and third foot adjustment plate fastener openings 44, 46, 48 thus holding and connecting the foot adjustment plate 20 to the connecting member 50. The second bent portion 62 defines first and second bent portion openings 72, 74.

It is to be understood that the fasteners 70 may be embodied as nuts and bolts, rivets 70a (shown with a dashed reference line in FIG. 6), screws, and in other suitable fasteners, and in other embodiments welds may be used instead of the fasteners 70. The connecting member 50 may be made of metal, aluminum, sheet steel, plastic, fiberglass and other suitable materials. In another embodiment, the foot adjustment plate 20 and connecting member 50 are formed as a one-piece body 74 as indicated by the dashed line in FIG. 6. For example, they could be formed from formed as a one piece body 74 made of molded plastic or fiberglass, or the foot adjustment plate 20 and connecting member 50 may be stamped from a sheet of metal and bent and drilled accordingly in manners well known to those having ordinary skill in the art.

The foot support assembly 12 also includes the above-mentioned shoe engagement component 52 that is adapted to engage the shoe 106 of the worker 100 wearing the knee brace 10 as shown in FIGS. 40-41. As shown in FIGS. 14-16 the shoe engagement component 52 has opposed first and second engagement component surfaces 82, 84, and the foot engagement component 80 has a connection portion 86 from which extend first and second leg portions 88, 90. As shown in FIGS. 15 and 16 the first and second leg portion 88, 90 are curved and the second engagement surface 84 has a foot engagement cushion layer 92 that is connected to the second engagement surface 84 with, for example, an adhesive 85. The adhesive 85 may be embodied as a waterproof adhesive.

The cushion layer 92 is adapted to abut against the shoe 106 of the worker 100 as shown in FIG. 40. The connection portion 86 defines first and second connection portion openings 94, 96. The first and second bent portion openings 72, 74 defined in the connecting member 50 are aligned with the first and second connection portion openings 94, 96 defined in the shoe engagement component 52 and fasteners 70, 70a (described above) are inserted therein and tightened to secure the connecting member 50 to the shoe engagement component 52. In anther one embodiment the connecting member 50 is secured to the shoe engagement component 52 with a weld.

FIGS. 17-27 show the knee support assembly 14 has a knee adjustment plate 110, and the knee adjustment plate has a first knee support surface 112 and an opposed second knee support surface 114. In one embodiment and as shown in FIG. 19-21 the first knee support surface 112 is convex and the second knee support surface 114 is concave as shown in FIGS. 19 and 20. In another embodiment the knee adjustment plate 110 is planar, that is it is flat. The knee adjustment plate 110 has opposed first and second end knee plate edges 116, 118, and opposed first and second knee plate edges 120, 122. The knee adjustment plate 110 also has opposed first and second slot edges 124, 126, and opposed third and fourth slot edges 128, 130 that together define a slot 132. The slot 132 extends along a second longitudinal axis designated LL that extends through the knee adjustment plate 110. A knee support padding layer 134 is joined to the second knee support surface 114 with an adhesive 85 that in one embodiment is a waterproof adhesive.

The knee adjustment plate 110 also defines a third strap bolt opening 138 and fourth strap bolt opening 140. The knee adjustment plate also defines a first knee adjustment plate fastener opening 142, a second knee adjustment plate fastener opening 144, and a third knee adjustment plate fastener opening 146 as shown in FIG. 19. As best shown in FIG. 17, third and fourth strap bolts 148, 150 are provided, and the third strap bolt 148 extends through the third strap bolt opening 138 and through a third first adjustment strap 152 and secures the third adjustment strap 152 to the knee adjustment plate 110. The fourth strap bolt 150 extends through the fourth strap bolt opening 140 and through a fourth adjustment strap 154 securing the fourth adjustment strap 154 to the knee adjustment plate 110. It is pointed out that the above described third and fourth strap bolts 148, 150 may be replaced with rivets 70a or other fastener 70. Each of the third and fourth adjustment straps 152, 154 are structurally the same and the third adjustment strap 152 has a loop portion 156 and a hook portion 158, and the fourth adjustment strap 154 has a loop portion 160 and a hook portion 162. The knee adjustment plate 110 may be made of metal, aluminum, sheet steel, plastic, fiberglass and other suitable materials.

The knee support assembly 14 further includes a knee pad connector component 166 having opposed first and second knee pad connector component ends 168, 170, and a knee pad connector bent portion 172 from which extend a knee plate connecting portion 174 and a pad connecting portion 176 as shown in FIGS. 22 and 23. The knee plate connecting portion 174 defines first, second and third knee plate connector openings 178, 180, 182, and the pad connecting portion 176 defines first and second pad connector openings 182, 184. The knee connector component 166 has opposed first and second knee connector component surfaces 188, 190. The knee connector component 166 is bent due to the knee connector bent portion 172 such that the first knee component surface 188 is folded in a direction such that the first knee pad component 188 is folded toward itself, or in other words, in on itself such that the pad connecting portion 176 is offset from the knee plate connecting portion 174.

The knee adjustment plate 110 is connected to the knee pad connector component 166 by aligning the first, second and third knee adjustment plate fastener openings 142, 144, 146 with the first, second and third knee plate connector openings 178, 180, 182 and using fasteners 70 or rivets 70a to secure them to one another. As previously described, the fasteners may be embodied as nuts and bolts, rivets, screws and other suitable fasteners known to those having ordinary skill in the art. In another embodiment the knee adjustment plate 110 and the knee pad connector component 166 may be secured to one another with a weld.

As best shown in FIGS. 1, 18 and 24-27 the knee support assembly 14 further includes a multilayer pad 192. The multilayer pad 192 has a ground contact layer 194, a support layer 196, a cushion layer 198 and a knee contact layer 200, and each of the layers has a rectangular shape, but could be differently shaped in other embodiments. The multilayer pad 192 has opposed first and second multilayer pad sides 193, 195, and opposed third and fourth multilayer pad sides. 197, 199, and opposed knee and ground sides multilayer pad sides 201, 203 as shown in FIG. 18. As shown in FIG. 26, the ground contact layer 194 has a ground contact surface 202 and an opposed bonding surface 204. The ground contact surface 202 will make contact with the floor or ground commonly indicated by reference number 111 when the knee brace 10 is used and thus the ground contact surface 202 may be embodied as a gripping surface 206 in one embodiment to prevent it from slipping on the ground or floor commonly designated by reference numeral 111 (FIGS. 40-41). As shown in FIGS. 17, 25 and 26, the gripping surface 206 may be in the form of protrusions 208, textures 209, hills and valleys indicated by reference numeral 210, tread patterns 212, raised pyramids other geometric structures commonly designated 214 and combinations thereof or virtually any other suitable shape. The ground contact layer 194 is made of rubber or crepe foam or foam or other suitable material. In addition, the ground contact layer 194 form may be made to have a white color, no color, or a tan color such that it will not leave marks on a floor 111 on which the worker 100 is working.

The support layer 196 has opposed convex and concave support layer sides 220, 222 and the support layer defines first and second support layer fastener openings 224, 226 as shown in FIG. 26. In other embodiments the support layer is flat. The support layer 196 is made of metal, for example aluminum, and in other embodiments may be made of stiff plastic, or fiberglass such that it will not readily flatten or deform. The support layer 196 is connected to the knee pad connector component 166 with fasteners 70 or a rivet 70a that extend through the first and second pad connector openings 182, 184 defined in the knee pad connector component 166 and the first and second support layer fastener openings 224, 226 defined in the support layer 196. As previously described the fasteners 70 may be bolt and nuts, rivets or the support layer 196 may be welded to the knee pad connector component 166. An adhesive 85, that may be in the form of a layer, is applied to the bonding surface 204 of the ground contact layer 192 and the convex support layer side 220 of the support layer 196 to hold and secure the ground contact layer 194 to the support layer 196.

Adhesive 85 is applied to the concave support layer side 220 of the support layer 196. The cushion layer 198 has opposed first and second cushion layer sides 228, 230, and the first cushion layer side 228 is moved against the concave support layer side 220 of the support side layer 196 and secured in place with adhesive 85.

Adhesive is applied to the second cushion layer side 230 of the cushion layer 198. The knee contact layer 200 has opposed first and second knee contact layer sides 232, 234. The second cushion layer side 230 is positioned against the first knee contact layer side 232 and secured in place with the adhesive 85. The knee contact layer 200 is a prosthetics gel liner layer 200a in one embodiment and as shown in FIG. 26 such that the knees 105 of the worker 100 are comfortable when kneeling on the floor 111. It is to be understood that the materials for the above-described pads may be varied in other embodiments.

FIG. 25 is a top view of the knee support assembly 14 showing the multilayer pad 192. As shown, the knee pad connector component 166 is embedded in the multilayer pad 192. FIG. 27 is a sectional view of the multilayer pad 192 and the knee pad connector component 166. As described above, the support layer 196 has opposed convex and concave support layer sides 220, 222, and this results in the ground multilayer pad side 203 of the multilayer pad 192 being convex and the opposed knee multilayer pad sides 201 being concave such that it can accommodate the knee 105 of the worker 100.

As shown in FIGS. 17 and 18, the knee pad connector component 166 is perpendicular to the knee adjustment plate 110 and the multilayer pad 192. In addition, as shown in FIG. 17, the connector component 166 is centrally positioned such that a first spacing distance designated D1 from the knee pad connector component 166 to the first multilayer pad side 193 is the same as a second spacing distance designated D2 that is the distance from the knee pad connector component 166 to the second multilayer pad side 195. When the worker 100 kneels on the multilayer pad 192 his or her knees rest on the knee contact layer 200. The above described knee support assembly 14 is suitable for use with either the left or right leg of the worker 100 because the multilayer pad 192 is centrally disposed relative to the knee pad connector component 166.

In another embodiment shown in FIGS. 17A and 17B the multilayer pads 192 are offset relative to the knee pad connector components 166. In this embodiment there is provided a left leg knee support assembly 14a and a right leg knee support assembly 14b. This accounts for the anatomical nature of human anatomy.

As shown in FIG. 17A, for the left leg knee support assembly 14a the first spacing distance designated D1 that is measured from the knee pad connector component 166 to the first multilayer pad side 193 is greater than the second spacing distance designated D2 that is the distance from the knee pad connector component 166 to the second multilayer pad side 195. For the right leg knee support assembly 14b the first spacing distance designated D1 that is measured from the knee pad connector component 166 to the first multilayer pad side 193 is less than the second spacing distance designated D2 that is the distance from the knee pad connector component 166 to the second multilayer pad side 195. Thus, the multilayer pads 192 are offset relative to the knee pad connecting components 166, and while at the same time the multilayer pads 192 are perpendicular to the knee pad connector components 166. The left and right leg knee support assemblies 14a, 14b result in the multilayer pads 192 mimicking or matching the natural offset of the left and right knees 105 of the worker 100. This results in a comfortable fit when the worker 100 supports his or her weight on his or her left and right knees that abut the knee contact layers 200 of the multilayer pads 192.

Shown in FIGS. 17C and 17D is another embodiment of the wherein the connector components 166 are replaced with a right offset knee pad connector component 167 (FIG. 17E) and a left offset knee pad connector component 169 (FIG. 17F).

As shown in FIG. 17C, the first spacing distance designated D1 that is measured from the right offset knee pad connector component 167 to the first multilayer pad side 193 is the same as the second spacing distance designated D2 that is the distance from the right offset knee pad connector component 167 to the second multilayer pad side 195. Similarly, the first spacing distance designated D1 that is measured from the left offset knee pad connector component 169 to the first multilayer pad side 193 is the same as the second spacing distance designated D2 that is the distance from the left offset knee pad connector component 169 to the second multilayer pad side 195.

The right offset knee pad connector component 167 has a left knee offset portion 171 and the left offset knee pad connector component 169 has right knee offset portion 173. This results in the multilayer pads 192 mimicking or matching or the natural offset of the left and right knees 105 of the worker 100. As previously described the knee adjustment plate 110 has opposed third and fourth knee plate edges 120, 122, and FIG. 17C shows the multilayer pad 192 is offset relative to the fourth knee plate edge 122 when connected to the right offset knee pad connecting component 167, and FIG. 17D shows the multilayer pad 192 is offset relative to the third knee plate edge 120 when connected to the left offset knee connecting component 169. This results in a comfortable fit when the worker 100 supports his or her weight on his or her left and right knees 105 that abut the knee contact layers 200 of the multilayer pads 192.

As shown in FIGS. 28-39 the calf engagement assembly 16 includes a calf brace 300 having opposed convex and concave calf brace surfaces 302, 304. The calf brace 300 has a peripheral edge 306 that extends from the convex calf brace surface 302 to the concave calf brace surface 304. In one of the embodiments the calf brace 300 has a first enlarged portion 310 that extends to a tapered portion 312 and the tapered portion 312 extends to a second enlarged portion 314, and wherein the first enlarged portion 310 is larger than the second enlarged portion 314. The calf brace 302 is made of plastic in one embodiment, but may also be made of metal, fiberglass, aluminum and combinations thereof. The concave calf brace surface 304 has supported on there a calf cushion 318 that is held in place with an adhesive 85, and the calf cushion 31 defines first, second, third and fourth calf cushion openings 319a, 319b, 319c, 319d, respectively, as shown in FIG. 29. The first enlarged portion 310 defines first and second strap fastener openings 311, 313, and the second enlarged portion 312 defines third and fourth strap fastener openings 315, 317, each of which is indicated in FIGS. 28 and 29 with dashed reference lines.

As shown in FIGS. 28, 30-37, the calf engagement assembly 16 also includes first, second, third and fourth strap connecting assemblies 320a, 320b, 320c, and 320d that are mounted on the calf brace 300 that are all structurally identical and are capable of pivoting. The first strap connecting assembly 320a includes a mounting bolt 322, a bolt washer 324, a strap engagement band 326 that defines first and second engagement fastener openings 334, 336, a strap connecting member 328 that defines first and second strap slots 329, 331, a strap engagement washer 330 and an assembly nut 332. The strap connecting member 328 may be made of leather, plastic, fabric, or other suitable material that is capable of being folded. In other preferred embodiments the mounting bolt 322 may be replaced with a rivet 70a or other suitable fastener. It is pointed out the first, second, third and fourth strap connecting assemblies 320a, 320b, 320c, and 320d are allowed to swivel, that is, they are capable of swiveling relative to the calf brace 300.

As shown in FIG. 28, the bolt washer 324 abuts against the concave brace surface 304, and the mounting bolt 322 extends through the bolt washer 324 and through the first strap fastener opening 311 defined in the calf brace 300, such that the mounting bolt head 323 abuts against the bolt washer 324. As shown, the bolt washer 324 is disposed in the first cushion opening 319a. The strap engagement band 326 is moved through the first strap slot 329 and folded in upon itself such that the first and second strap connector fastener openings 334, 336 are aligned. The mounting bolt 322 extends through the aligned first and second strap connector fastener openings 334, 336. The strap engagement washer 330 is fitted on the mounting bolt 322 and the assembly nut 332 is threaded to the mounting bolt 322 and tightened such that the first strap connecting assembly 320a is secured to the calf brace 300. As shown in FIGS. 28 and 29, the second, third and fourth strap connecting assemblies 320b, 320c and 320d are mounted on the calf brace 300 in an identical manner and are arranged such the first and second strap connecting assemblies 320a, 320b are mounted on the first enlarged portion 310 and the third and fourth strap connecting assemblies 320c, 320d are mounted on the second enlarged portion 314.

Figure 5A:
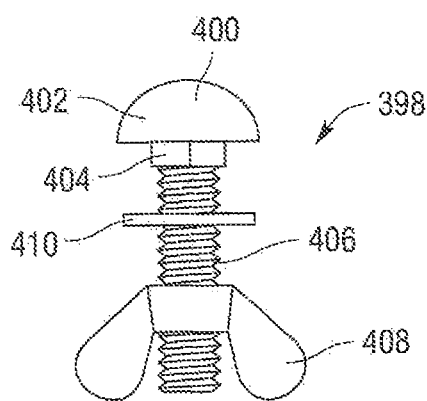
FIG. 5A is a front view of an adjustment bolt assembly.

As shown in FIGS. 1, 2, 3, 4, 5, and 40-41, the foot adjustment plate 20 is adjustable relative to the knee adjustment plate 110 such that the length of the knee brace 10 can be increased and decreased to accommodate the leg of the worker 100 regardless of the height of the worker 100. To accomplish this, the adjustment bolt assemblies commonly designated by reference number 398 and shown in FIG. 5A are provided and shown in FIG. 5A, and two adjustment bolt assemblies 398 are shown and used in one of the embodiments. Each adjustment bolt assembly 398 includes an adjustment bolt 400 having a convex shaped head 402, a square neck 404, and a threaded portion 406 that extends from the convex shaped head 402. Each adjustment bolt assembly 398 also includes a wing nut 408 and an adjustment bolt washer 410, and the wing nut 408 is capable of being threaded to the threaded portion 406 of the adjustment bolt 400. The foot adjustment plate 20 is aligned with the knee adjustment plate 110 such that the second foot adjustment surface 26 of the foot adjustment plate 20 abuts the first knee support surface 112 of the knee adjustment plate 110, and the pair of spaced apart square shaped adjustment bolt openings 28, 30 defined in the foot adjustment plate 20 align with the slot 132 defined in the knee adjustment plate 110. The threaded portions 406 of the adjustment bolts 400 are moved through slot 132 and through the square shaped adjustment bolt openings 28, 30 defined in the foot adjustment plate 20 such that the threaded portions 406 extend from the foot adjustment plate 20. The square necks 404 of the adjustment bolts 400 abut the first slot edge 124 and the second slot edge 126 that define the slot 132 in the knee adjustment plate 110. The adjustment bolt washers 410 are moved over the threaded portions 406 and the wing nuts 408 are threaded to the threaded portions 406 of the adjustment bolts 400. At this point, that is, prior to tightening the wing nuts 408 the knee adjustment plate 110 can be slid or moved relative to the foot adjustment plate 20 to lengthen or shorten the knee brace 10 as indicated by the arrows designated A and B in FIG. 4. In one preferred embodiments the adjustment plate 110 can be slid or moved relative to the foot adjustment plate 20 about four inches, but could be more or less depending on the length of the slot 132. Thus, the knee brace 10 can have a first length designated L1 in FIG. 4 and a second length designated L2 in FIG. 2 that is less than the first length designated L1. As shown in FIG. 2, when the knee brace 10 is in a contracted position 420 the multilayer knee pad 192 is as close as possible to the shoe engagement component 52 as indicated by X1 in FIG. 2. The knee brace 10 is extendable to an extended position wherein distance from the multilayer knee pad 192 to the shoe engagement component 52, indicated by X2 in FIG. 4, is greater than X1. Thus, the knee brace 10 is capable of being worn and used by all workers 100 regardless of their height or the length of their leg 102, calf 101 and shin 103 because the workers 100 can adjust the foot adjustment plate 20 relative to the knee adjustment plate 110 prior to tightening the wing nuts 408. In other embodiments the wing nuts 408 may be replaced with nuts.

In use, the worker 100 takes the knee brace 10 and positions the multilayer pad 192 against his or her knee 105, and positions his or her shoe 106 such that it is proximal the shoe engagement component 52. The worker then adjusts the foot adjustment plate 20 relative to the knee adjustment plate 110 until he or she determines a proper fit, that is, when the shoe 106 engages the shoe engagement component 52 and the multilayer pad 192 feels comfortable and like a suitable fit. Then the worker 100 tightens the wing nuts 408 such that the adjustment bolts 400 are secured in place, thus fixing the position of the foot adjustment plate 20 relative to the knee adjustment plate 110. Next, the worker 100 has to secure the calf brace 300 to the foot adjustment plate 20 and the knee adjustment plate 110. The worker 100 moves the first enlarged portion 310 of the calf brace such that it is proximal the calf 101 of the worker 100 and moves the second enlarged portion 314 such that it is proximal the shoe 106.

Then, as shown in FIG. 38 and FIG. 39 the adjustment straps are connected to the calf engagement assembly 16. The worker 100 moves the calf brace 300 such that it abuts his or her calf 101 and moves the fourth adjustment strap 154 through the second strap slot 331 defined in the strap connecting member 328 of the first strap connecting assembly 320a (as indicated by the arrow designated T in FIG. 38). Then, the fourth adjustment strap 154 is folded over on itself (as indicated by the arrow designated V in FIG. 39) itself such that the hook portion 162 engages the loop portion 160 thus securing the hook portion 162 and the loop portion 160 to one another (as indicated by the arrow designated V in FIG. 39), while at the same time securing the fourth adjustment strap 154 to the first strap connecting assembly 320a. In an identical manner, the first adjustment strap 45 is moved through the strap connector member 328 of the fourth strap connector assembly 320d and folded in upon itself, and the second adjustment strap 47 is moved through the strap connector member 328 of the third strap connector assembly 320c and folded in upon itself, and the third adjustment strap 152 is moved through the strap connector member 328 of the second strap connector assembly 320b and folded in upon itself. Thus, after the first, second, third and fourth adjustment straps 45, 47, 152, 154 are secured in this manner the calf engagement assembly 16 is secured to the foot support assembly 12, the knee support assembly 14 such that the knee brace is secured to the leg 102 of the worker 100. The worker 100 can then adjust the first, second, third and fourth adjustment straps 45, 47, 152, 154 until he or she finds a comfortable fit.

The worker 100 is able to kneel for extended periods of time when wearing the knee brace 10 because the multilayer pads 192 provides for comfort and protection from the surrounding environment. In addition, the calf brace 300 and shoe engagement component 52 secure the knee brace 10 to the leg of the worker 100 while he or she is working or walking. Also, the knee brace 10 does not move relative to the leg of the worker 100 while crawling or moving on the floor 111. The knee brace 10, because it is adjustable by the worker 100, will not cut off blood circulation in the legs 102 or otherwise cause the worker 100 to experience pain or discomfort when worn. Also, the calf engagement assembly 16 self adjusts as the worker 100 moves because the first, second, third and fourth strap connector assemblies 320a-320d are capable of pivoting.

It will be appreciated by those skilled in the art that while the knee brace 10 has been described in detail herein, the knee brace 10 is not necessarily so limited and other examples, embodiments, uses, modifications, and departures from the embodiments, examples, uses, and modifications may be made without departing from the knee brace 10, and all such embodiments are intended to be within the scope and spirit of the appended claims.

What is claimed:
1. A knee brace comprising:
a foot support assembly;
a knee support assembly and wherein the foot support assembly is adjustable relative to the knee support assembly;
a calf engagement assembly having a calf brace and wherein the calf engagement assembly is connected to the foot support assembly and the knee support assembly;
wherein the foot support assembly further includes a foot adjustment plate and first and second adjustment straps are connected to the foot adjustment plate; and,
the foot support assembly includes a connecting member that connects the foot adjustment plate to a shoe engagement component that is adapted to contact a shoe.
2. The knee brace according to claim 1 wherein the first and second adjustment straps are for connecting the foot support assembly to the calf engagement assembly.
3. The knee brace according to claim 1 wherein the knee support assembly further includes a knee adjustment plate and third and fourth adjustment straps that are connected to the knee adjustment plate, and a knee pad connector component is connected to the knee adjustment plate and the knee pad connector component is connected to a multilayer pad and wherein the multilayer pad is adapted to support the knee of a worker.
4. The knee brace according to claim 3 wherein the third and fourth adjustment straps are for connecting the third and fourth adjustment straps to the calf engagement assembly.
5. The knee brace according to claim 3 wherein the foot adjustment plate defines first and second adjustment bolt openings and the knee adjustment plate defines a slot and the first and second adjustment bolt openings are aligned with the slot and adjustment bolts are provided having square necks from which extend threaded portions wherein the square necks are fitted in the slot and the threaded portion extend through the first and the treaded portions extend though the bolt openings and a nut is threaded to the threads and that the foot adjustment plate and the knee adjustment plate can be moved relative to one another prior to tightening the nut and upon tightening the nut position of the foot adjustment plate relative to the knee adjustment plate fixed in place.
6. The knee brace according to claim 3 wherein the multilayer pad has a ground contact layer that is supported on and adhered to a support layer that is supported on and adhered to a cushion layer that is supported on and adhered to a knee contact layer and the support layer is connected to the knee pad connector component and the support layer has opposed convex and concave support layer sides such that the multilayer pad has a convex side and concave side and wherein the convex side is adapted to support a knee and the convex side is adapted to contact a ground.
7. The knee brace according to claim 6 wherein the ground contact layer has a gripping surface and the knee contact layer is a prosthetics gel liner layer.
8. The knee brace according to claim 3 wherein the calf engagement assembly further includes a calf brace having first and second enlarged portions wherein the first enlarged portion is larger than the second enlarged portion and wherein first and second strap connecting assemblies are mounted on the first enlarged portion and third and fourth strap connecting assemblies are mounted on the second enlarged portions and the fourth adjustment strap is positioned in the first strap connecting assembly, and the third adjustment strap is positioned in the second strap connecting assembly, and the first adjustment strap is positioned in the third strap connecting assembly, and the second adjustment strap is positioned in the fourth connecting assembly.
9. The knee brace according to claim 8 wherein each of the first, second, third and fourth adjustment straps has a hook portion and a loop portion, and each of the first, second, third and fourth strap connecting assemblies has a strap connector member such that each of the first, second, third and fourth adjustment straps can be folded over the strap connector members such that the hooks portions engage the loop portions in order to releasably secure the knee and foot adjustment plates to the calf brace.
10. The knee brace according to claim 1 wherein the knee support assembly further includes a knee adjustment plate having opposed first and second knee plate edges and opposed third and fourth knee plate edges and third and fourth adjustment straps that are connected to the knee adjustment plate, and a right offset knee pad connector component is connected to the knee adjustment plate and the right offset knee pad connector component is connected to a multilayer pad and wherein multilayer pad has opposed first and second multilayer pad sides and opposed third and fourth multilayer pad sides and opposed knee and ground multilayer pad sides, and the right offset knee pad connector component extends from the fourth multilayer pad side such that a first distance measured from the first multilayer pad side to the right offset knee pad connector is equal to a second distance measured from the second multilayer pad side to the first offset knee pad connector component, and wherein the multilayer pad is offset relative to the fourth knee plate edge when connected to the right offset knee pad connecting component.
11. The knee brace according to claim 1 wherein the knee support assembly further includes a knee adjustment plate having opposed first and second knee plate edges and opposed third and fourth knee plate edges and third and fourth adjustment straps that are connected to the knee adjustment plate, and a left offset knee pad connector component is connected to the knee adjustment plate and the left offset knee pad connector component is connected to a multilayer pad and wherein multilayer pad has opposed first and second multilayer pad sides and opposed third and fourth multilayer pad sides and opposed knee and ground multilayer pad sides, and the left offset knee pad connector component extends from the fourth multilayer pad side such that a first distance measured from the first multilayer pad side to the left offset knee pad connector is equal to a second distance measured from the second multilayer pad side to the left offset knee pad connector component, and wherein the multilayer pad is offset relative to the fourth knee plate edge when connected to the left offset knee pad connecting component.

* * * * *